United States Patent
Keffeler et al.

(10) Patent No.: US 10,639,093 B2
(45) Date of Patent: May 5, 2020

(54) SURGICAL INSTRUMENT INCLUDING A WIRE GUIDE

(71) Applicant: COVIDIEN LP, Mansfield, MA (US)

(72) Inventors: David M. Keffeler, Niwot, CO (US); Kris Hess, Nederland, CO (US)

(73) Assignee: COVIDIEN LP, Mansfield, MA (US)

( * ) Notice: Subject to any disclaimer, the term of this patent is extended or adjusted under 35 U.S.C. 154(b) by 695 days.

(21) Appl. No.: 15/366,045

(22) Filed: Dec. 1, 2016

(65) Prior Publication Data

US 2018/0153614 A1    Jun. 7, 2018

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/00178* (2013.01); *A61B 2018/00607* (2013.01); *A61B 2018/1455* (2013.01)

(58) Field of Classification Search
CPC .............................................. A61B 2018/0091
See application file for complete search history.

(56) References Cited

U.S. PATENT DOCUMENTS

| | | | |
|---|---|---|---|
| 5,318,526 A | | 6/1994 | Cohen |
| 5,327,905 A | * | 7/1994 | Avitall ............... A61B 18/1492 600/381 |
| 5,458,598 A | * | 10/1995 | Feinberg ............ A61B 18/1445 606/205 |
| 5,605,272 A | | 2/1997 | Witt et al. |
| 5,609,573 A | * | 3/1997 | Sandock ............. A61B 18/1482 604/22 |
| 5,792,139 A | * | 8/1998 | Chambers .......... A61B 18/1482 606/41 |

(Continued)

FOREIGN PATENT DOCUMENTS

| | | |
|---|---|---|
| AU | 2004216575 A1 | 4/2005 |
| CA | 2844067 A1 | 9/2014 |
| EP | 2319447 A1 | 5/2011 |

OTHER PUBLICATIONS

Partial European Search Report issued in corresponding European application No. 16170578.5 dated Sep. 1, 2016.

(Continued)

*Primary Examiner* — Ronald Hupczey, Jr.
(74) *Attorney, Agent, or Firm* — Carter, DeLuca & Farrell LLP (57) ABSTRACT

A surgical instrument including a housing, a shaft, an end effector assembly, a first electrical wire, and a wire guide. The shaft defines a lumen and extends distally from the housing. The end effector assembly is disposed at a distal end portion of the shaft and includes a first electrically-conductive tissue-treating surface. The first electrical wire extends from the housing, through the shaft, and into electrical communication with the first electrically-conductive tissue-treating surface. The electrical wire is adapted to connect to a source of energy and configured to supply energy to the first electrically-conductive tissue-treating surface. The wire guide is disposed within the housing and engaged about a proximal portion of the shaft within the housing. The wire guide is also configured to guide the first electrical wire from the housing into the shaft.

17 Claims, 7 Drawing Sheets

(56) References Cited

U.S. PATENT DOCUMENTS

| | | | |
|---|---|---|---|
| 5,891,142 A | 4/1999 | Eggers et al. | |
| 5,919,206 A | 7/1999 | Gengler et al. | |
| 5,921,983 A * | 7/1999 | Shannon, Jr. | A61B 18/1442 606/45 |
| 5,935,126 A | 8/1999 | Riza | |
| 6,045,549 A * | 4/2000 | Smethers | A61B 18/1477 604/22 |
| 6,077,287 A | 6/2000 | Taylor et al. | |
| 6,129,740 A | 10/2000 | Michelson | |
| 6,322,579 B1 | 11/2001 | Muller | |
| 6,334,860 B1 | 1/2002 | Dorn | |
| 6,443,968 B1 | 9/2002 | Holthaus et al. | |
| 6,506,208 B2 | 1/2003 | Hunt et al. | |
| 6,706,056 B2 | 3/2004 | Bacher | |
| 6,770,072 B1 | 8/2004 | Truckai et al. | |
| 6,790,217 B2 | 9/2004 | Schulze et al. | |
| 6,887,240 B1 | 5/2005 | Lands et al. | |
| 7,052,496 B2 | 5/2006 | Yamauchi | |
| 7,147,638 B2 | 12/2006 | Chapman et al. | |
| 7,150,097 B2 | 12/2006 | Sremcich et al. | |
| 7,331,947 B2 * | 2/2008 | McGuckin, Jr. | A61B 18/00 604/506 |
| 7,384,420 B2 | 6/2008 | Dycus et al. | |
| 7,494,501 B2 | 2/2009 | Ahlberg et al. | |
| 7,549,988 B2 | 6/2009 | Eberl et al. | |
| 7,559,940 B2 | 7/2009 | McGuire et al. | |
| 7,753,909 B2 | 7/2010 | Chapman et al. | |
| 7,758,608 B2 | 7/2010 | DiCesare et al. | |
| 7,766,910 B2 | 8/2010 | Hixson et al. | |
| 7,877,853 B2 | 2/2011 | Unger et al. | |
| 7,922,953 B2 | 4/2011 | Guerra | |
| 8,241,320 B2 | 8/2012 | Lyons et al. | |
| 8,252,021 B2 | 8/2012 | Boulnois et al. | |
| 8,266,783 B2 | 9/2012 | Brandt et al. | |
| 8,388,646 B2 | 3/2013 | Chojin | |
| 8,394,094 B2 | 3/2013 | Edwards et al. | |
| 8,409,244 B2 | 4/2013 | Hinman et al. | |
| 8,545,534 B2 | 10/2013 | Ahlberg et al. | |
| 8,551,090 B2 | 10/2013 | Sutter et al. | |
| 8,728,118 B2 | 5/2014 | Hinman et al. | |
| 8,740,933 B2 | 6/2014 | Anderson | |
| 8,789,741 B2 | 7/2014 | Baxter, III et al. | |
| 8,814,856 B2 | 8/2014 | Elmouelhi et al. | |
| 8,858,553 B2 | 10/2014 | Chojin | |
| 9,149,324 B2 | 10/2015 | Huang et al. | |
| 2004/0030330 A1 * | 2/2004 | Brassell | A61B 18/1206 606/41 |
| 2005/0090837 A1 | 4/2005 | Sixto et al. | |
| 2010/0063525 A1 | 3/2010 | Beaupre et al. | |
| 2011/0270251 A1 | 11/2011 | Horner et al. | |
| 2014/0025073 A1 | 1/2014 | Twomey et al. | |
| 2016/0338718 A1 | 11/2016 | Allen, IV et al. | |
| 2016/0338719 A1 | 11/2016 | Allen, IV et al. | |
| 2016/0338762 A1 | 11/2016 | Krastins et al. | |
| 2016/0338763 A1 | 11/2016 | Allen, IV et al. | |
| 2016/0338764 A1 | 11/2016 | Krastins et al. | |

OTHER PUBLICATIONS

Extended European search report issued in corresponding application No. 16170578.5 dated Dec. 5, 2016.

* cited by examiner

SURGICAL INSTRUMENT INCLUDING A WIRE GUIDE

BACKGROUND

Technical Field

The present disclosure relates to surgical instruments, more particularly, to a surgical instrument including a wire guide configured to guide one or more wires from a housing of the surgical instrument into a shaft thereof.

Background of Related Art

A surgical forceps is a plier-like device which relies on mechanical action between its jaws to grasp, clamp, and constrict tissue. Energy-based surgical forceps utilize both mechanical clamping action and energy to treat, e.g., coagulate, cauterize, and/or seal, tissue. Typically, once tissue is treated, the surgeon has to accurately sever the tissue.

Currently, energy-based surgical forceps are designed to include one or more hollow or semi-hollow housings, which typically house and/or operably couple to a shaft supporting an end effector assembly, a handle assembly, a trigger assembly, a drive assembly, an energy activation assembly, and one or more electrical wires which extend through the housing and shaft to supply energy to the end effector assembly of the energy-based surgical forceps for treating tissue therewith. It is important to inhibit the electrical wires from potential damage as well as from interfering with the above-noted and other components of the forceps. Protecting electrical wires in other surgical instruments from damage and/or interference with components of the surgical instrument is likewise important.

SUMMARY

A surgical instrument provided in accordance with aspects of the present disclosure includes a housing, a shaft extending distally from the housing and defining a lumen therethrough, an end effector assembly disposed at a distal end portion of the shaft, a first electrical wire, and a wire guide. The end effector includes a first electrically-conductive tissue-treating surface. The first electrical wire extends from the housing, through the shaft, and into electrical communication with the first electrically-conductive tissue-treating surface. Also, the first electrical wire is adapted to connect to a source of energy and configured to supply energy to the first electrically-conductive tissue-treating surface. The wire guide is disposed within the housing and engaged about a proximal portion of the shaft within the housing. The wire guide is also configured to guide the first electrical wire from the housing into the shaft.

In an aspect of the present disclosure, the wire guide includes at least one guiding feature configured to receive the first electrical wire and guide the first electrical wire along the wire guide.

In another aspect of the present disclosure, the wire guide includes a plurality of guiding features spaced-apart on the wire guide.

In another aspect of the present disclosure, the wire guide further includes a shaft attachment, which is engaged about the proximal end of the shaft. The shaft attachment has a proximal end portion and distal end portion, wherein the proximal end portion of the shaft attachment includes a wire snap feature. The wire snap feature is configured to guide the first electrical wire from the wire guide into the shaft. The shaft attachment further defines a shaft passageway including a first end and a second end, and wherein the wire snap feature is disposed adjacent the first end of shaft passageway.

In another aspect of the present disclosure, the surgical instrument includes a second electrical wire extending from the housing, through the shaft, and into electrical communication with a second electrically-conductive tissue-treating surface of the end effector assembly. The second electrical wire adapted to connect to a source of energy and configured to supply energy to the second electrically-conductive tissue treating surface, wherein the wire guide is configured to guide the second electrical wire from the housing into the shaft. The wire guide includes at least one guiding feature, each guiding feature configured to receive each of the first and second electrical wires. The wire guide also includes a first and second wire snap features. The first wire snap feature is configured to receive the first electrical wire and the second wire snap feature configured to receive the second electrical wire. The first and second wire snap features are spaced-apart to maintain the first and second electrical wires in spaced-apart relation in the vicinity of the first and second wire snap features. Further, the first and second wire snap features are disposed adjacent a proximal end of the shaft.

In another aspect of the present disclosure, the wire guide includes a housing attachment. The housing attachment engaging the wire guide to the housing.

In another aspect of the present disclosure, the surgical instrument includes a housing, a shaft extending distally from the housing and defining a lumen therethrough, an end effector assembly disposed at a distal end portion of the shaft, a first electrical wire extending from the housing, through the shaft, and into electrical communication with the end effector assembly, and a wire guide. The wire guide is disposed within the housing. The wire guide includes a body, a plurality of spaced-apart wire guiding features, a shaft attachment, and a first wire snap feature. The body includes a proximal end portion and a distal end portion, wherein the plurality of spaced-apart wire guiding features are disposed on the body between the proximal and distal portions thereof. The shaft attachment is disposed at the distal end portion of the body and is engaged about the shaft. The first wire snap feature is disposed on the shaft attachment. The plurality of spaced-apart wire guiding features are configured to guide the first electrical wire along the body of the wire guide from the proximal end portion thereof to the distal end portion thereof, and wherein the first wire snap feature is configured to guide the first wire from the body of the wire guide into the shaft.

In another aspect of the present disclosure, the surgical instrument includes a second electrical wire extending from the housing, through the shaft, and into electrical communication with the end effector assembly. The wire guide is configured to guide the second electrical wire from the housing into the shaft. The plurality of spaced-apart wire guiding features is configured to receive each of the first and second electrical wires. The wire guide also includes a second wire snap feature. The first wire snap feature is configured to receive the first electrical wire and the second wire snap feature is configured to receive the second electrical wire. The first and second wire snap features are spaced-apart to maintain the first and second electrical wires in spaced-apart relation to the vicinity of the first and second wire snap features. The wire guide also includes a housing attachment. The housing attachment engages the wire guide to the housing.

BRIEF DESCRIPTION OF THE DRAWINGS

Various aspects and features of the present disclosure are described hereinbelow with reference to the drawings wherein.

DETAILED DESCRIPTION

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

Figure 1:
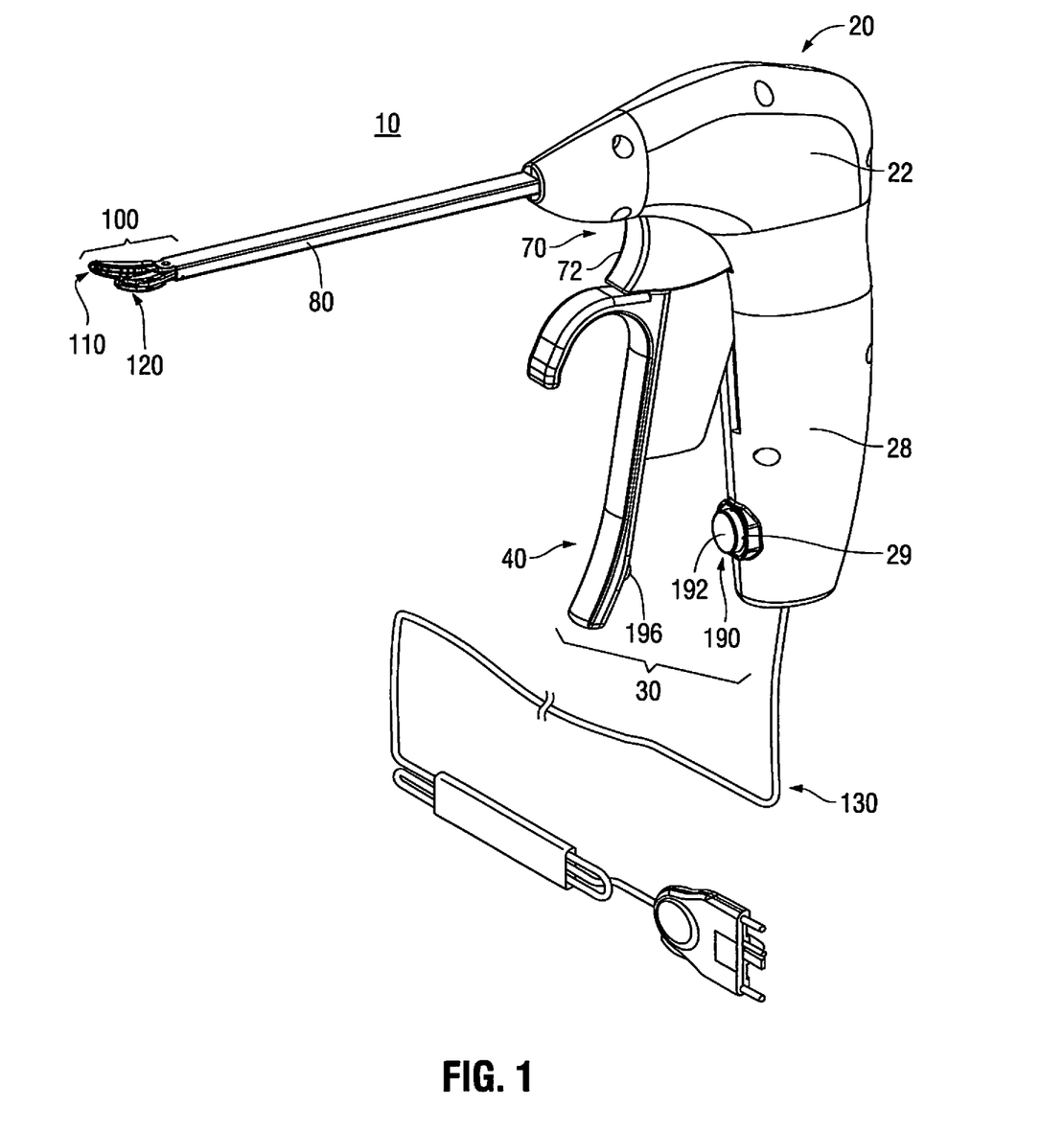
FIG. 1 is a front, perspective view of a surgical instrument provided in accordance with the present disclosure with jaw members of an end effector assembly of the surgical instrument disposed in a spaced-apart position.

Referring generally to FIG. 1, a surgical instrument provided in accordance with the present disclosure is shown generally identified by reference numeral 10. Instrument 10 is configured for grasping, treating, and/or dissecting tissue. Additional features contemplated for use with instrument 10 are detailed in commonly-owned U.S. patent application Ser. Nos. 14/719,422, 14/719,434, 14/719,452, 14/719,464, and 14/719,475, each of which was filed on May 22, 2015, and is incorporated herein by reference in its entirety. Although the aspects and features of the present disclosure are detailed with respect to instrument 10, such aspects and features are likewise applicable for use with any other suitable surgical instrument. For the purposes herein, instrument 10 is generally described.

Figure 2:
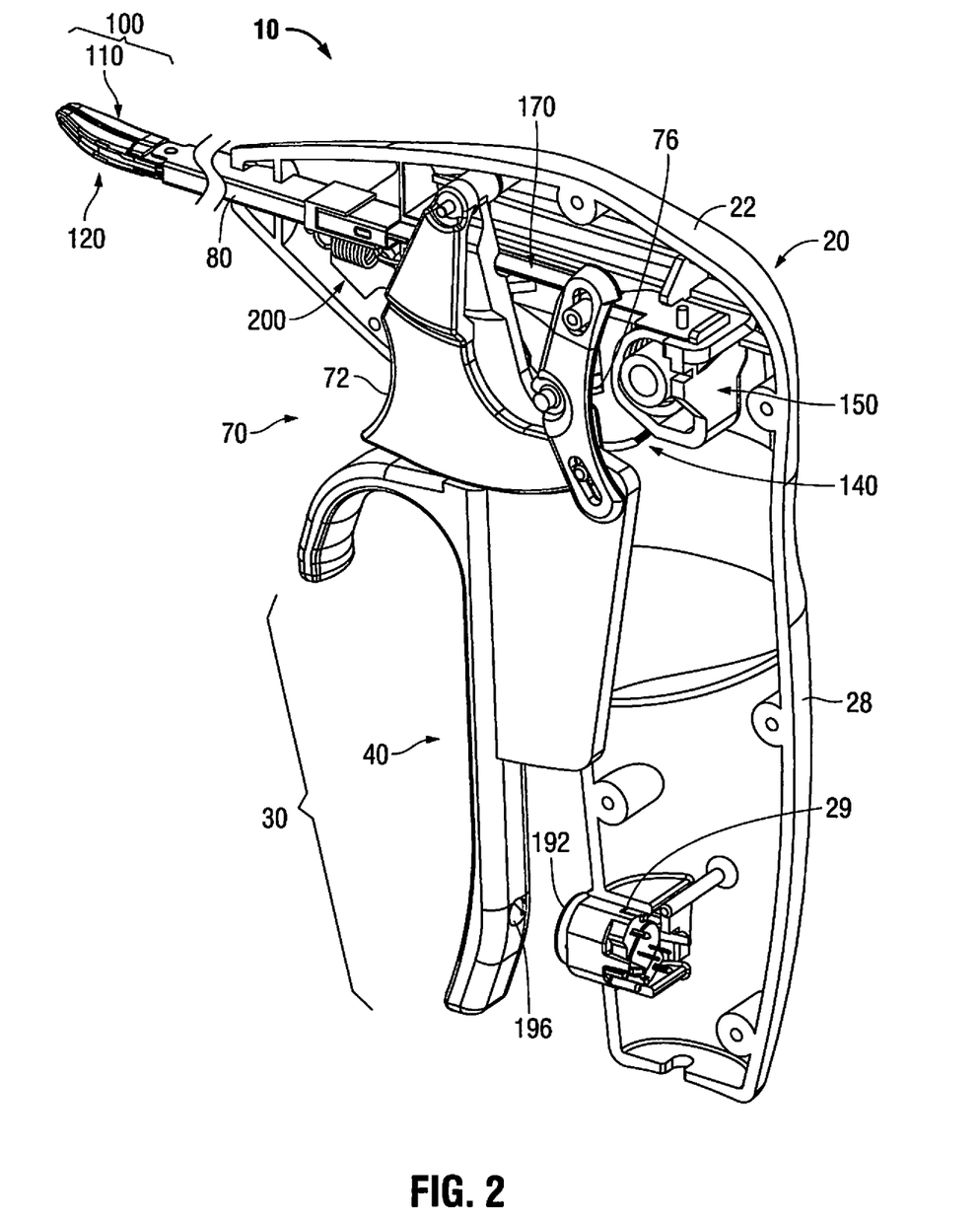
FIG. 2 is a rear, perspective view of the surgical instrument of FIG. 1 with the jaw members disposed in an approximated position and a portion of a housing of the surgical instrument removed to illustrate the internal components therein.

With reference to FIGS. 1 and 2, instrument 10 generally includes a housing 20, a handle assembly 30, a trigger assembly 70, a shaft 80, a wire guide 200, an end effector assembly 100, a drive assembly 140, a knife assembly 170, and an energy activation assembly 190.

Housing 20 houses the internal working components of instrument 10 and is formed from first and second housing components configured to engage one another via a plurality of pin-aperture engagements spaced around an outer perimeter of the housing 20, although other suitable engagements, e.g., screws, snap-fit connections, adhesion, ultrasonic welding, etc., are also contemplated, as are different formations of housing 20. Housing 20 defines a pistol-style configuration having a longitudinally-extending barrel portion 22 and a fixed handle portion 28 that extends from barrel portion 22 in generally perpendicular orientation relative thereto.

Figure 7:
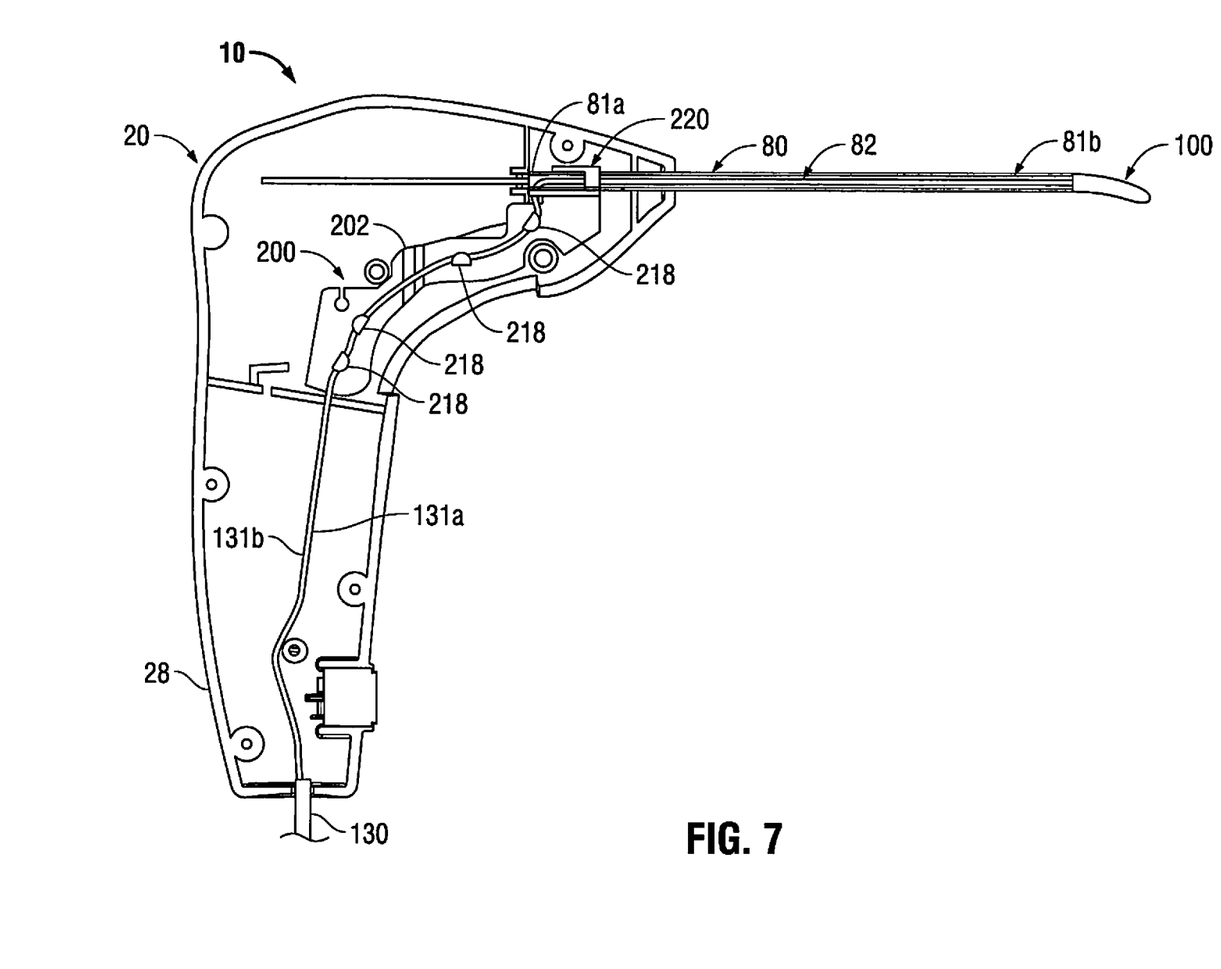
FIG. 7 is another side view of the proximal portion of the surgical instrument of FIG. 1 with components removed to illustrate the wire guide of FIG. 6 operably coupled to the housing and the shaft and shown guiding wires from the housing into the shaft.
Figure 8:
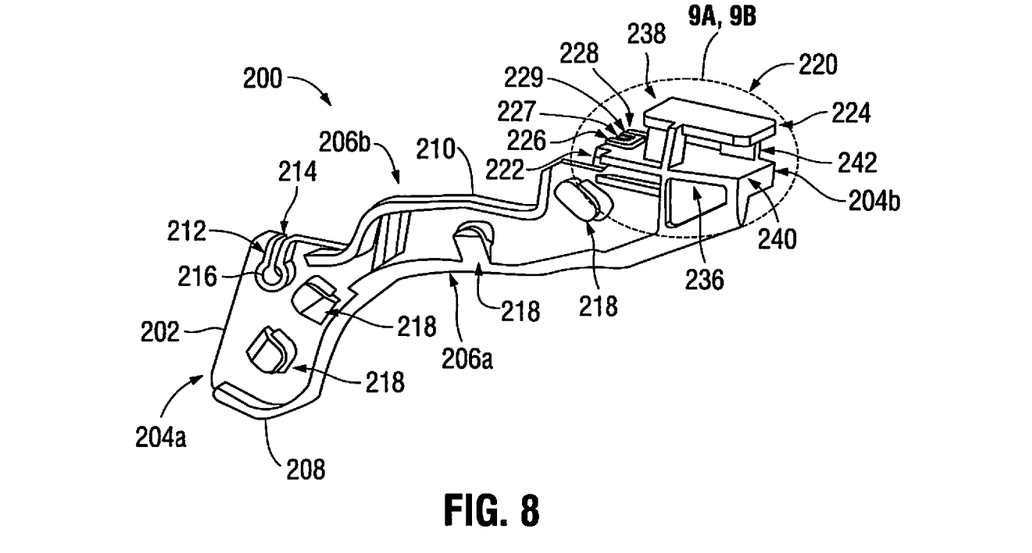
FIG. 8 is perspective view of the wire guide of FIG. 6.

With momentary additional reference to FIG. 7, shaft 80 extends distally from housing 20 and defines a proximal end portion 81a, a distal end portion 81b, and a lumen 82 extending longitudinally therethrough. Proximal end portion 81a of shaft 80 is engaged to housing 20, while distal end portion 81b of shaft 80 supports end effector assembly 100. Lumen 82 provides a pathway for drive assembly 140, first electrical wire 131a, and second electrical wire 131b from housing 20 to end effector assembly 100.

Referring again to FIGS. 1 and 2, handle assembly 30 includes a movable handle 40 that is movable relative to fixed handle portion 28 of housing 20 between an initial position, a compressed position, and an activated position to impart movement of jaw members 110, 120 of end effector assembly 100 between a spaced-apart position and an approximated position for grasping tissue therebetween and for initiating the supply of energy to end effector assembly 100 for treating grasped tissue. Drive assembly 140 operably couples handle assembly 30 with end effector assembly 100 to enable selective manipulation of jaw members 110, 120 of end effector assembly 100 via actuation of movable handle 40. More specifically, briefly referring also to FIG. 5, drive assembly 140 includes a drive plate 142 and a slider assembly 150. Drive plate 142 extends distally from housing 20 and through shaft 80 to operably engage end effector assembly 100, while slider assembly 150 operably couples drive plate 142 and movable handle 40 with one another such that actuation of movable handle 40 translates drive plate 142 through shaft 80 and relative to end effector assembly 100 to pivot jaw members 110, 120 of end effector assembly 100 between the spaced-apart and approximated positions.

With continued reference to FIG. 2, knife assembly 170 is operably coupled with trigger assembly 70 to enable selective translation of a knife blade (not shown) of knife assembly 170 relative to end effector assembly 100 via actuation of trigger assembly 70. Trigger assembly 70, more specifically, includes a trigger 72 and a linkage 76. Linkage 76 serves to operably couple trigger 72 with knife assembly 170 such that pivoting of trigger 72 from the un-actuated position to the actuated position advances the knife blade between jaw members 110, 120 of end effector assembly 100 to cut tissue grasped therebetween.

Energy activation assembly 190 enables energy to be selectively delivered to end effector assembly 100. Energy activation assembly 190, more specifically, includes a depressible button 192 that is mechanically coupled to a switch 194 mounted within a bay 29 defined within fixed handle portion 28 of housing 20 and is engagable by a button activation post 196 extending proximally from a proximal side of movable handle 40 upon movement of movable handle 40 to the activated position. Switch 194 is configured to electrically communicate with end effector assembly 100 and a generator or other suitable energy source (not shown) via the first and second electrical wires 131a, 131b extending through housing 20 and shaft 80 to enable energy to be supplied from the generator to end effector assembly 100 upon activation of switch 194.

Wire guide 200 guides first electrical wire 131a and second electrical wire 131b through the housing 20 and into shaft 80 in order to operably couple the generator with energy activation assembly 190 and end effector assembly 100 to enable the selective supply of energy to the end effector assembly 100 via actuation of energy activation assembly 190. Wire guide 200 is described in greater detail hereinbelow.

Figure 3:
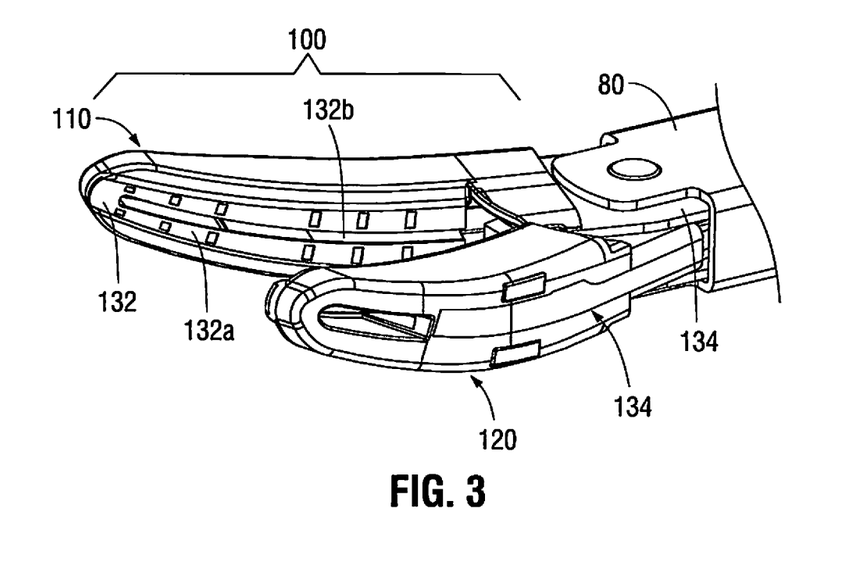
FIG. 3 is a perspective view of the distal end of the surgical instrument of FIG. 1 with the jaw members disposed in the spaced-apart position.
Figure 4:
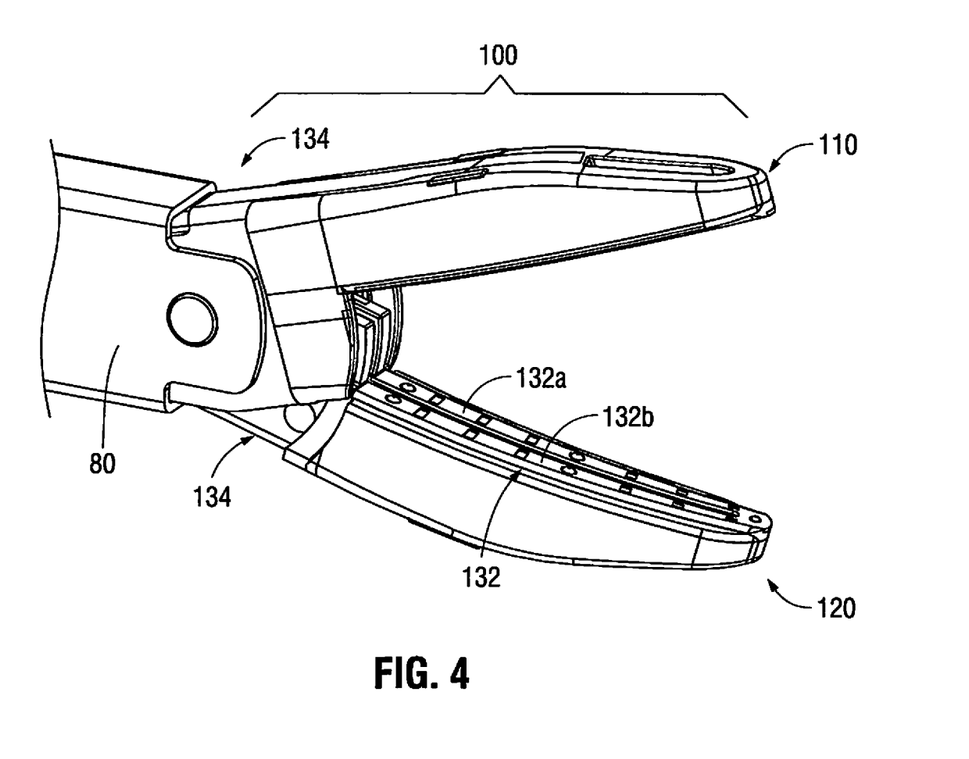
FIG. 4 is another perspective view of the distal end of the surgical instrument of FIG. 1 with the jaw members disposed in the spaced-apart position.

With reference to FIGS. 3 and 4, as mentioned above, end effector assembly 100 is operably supported at the distal end portion 81b of shaft 80 (FIG. 7). End effector assembly 100 includes opposing jaw members 110, 120 pivotably coupled to one another and movable relative to one another and shaft 80 between a spaced-apart position and an approximated position for grasping tissue therebetween, although unilateral configurations are also contemplated. Each jaw member 110, 120 includes an electrically-conductive plate 132 and an insulative jaw housing 134. The electrically-conductive plate 132 of each jaw member 110, 120 defines a generally planar tissue-contacting surface 132a and an elongated knife slot 132b extending through the respective tissue-contacting surface 132a.

With reference to FIGS. 5-9b, the wire guide 200 includes a body 202, a housing attachment 212, plurality of guiding features 218, and a shaft attachment 220. Body 202 defines a configuration that generally conforms to a portion of housing 20, such as a portion of the inner, concave elbow of the pistol-style configuration of housing 20. The body 202 includes a proximal portion 204a and a distal portion 204b. The proximal portion 204a is aligned with a portion of the fixed handle portion 28 of the housing 20 and the distal portion 204b is aligned with a portion of the barrel portion 22 of the housing 20. The body 202 thus extends from fixed handle portion 28 of housing 20, along the concave elbow of the pistol-style configuration of housing 20, and to the barrel portion 22 of housing 20.

The body 202 further includes a first side 206a and a second side 206b. The first side 206a includes a first spine 208 perpendicularly protruding therefrom. The first spine 208 provides secondary security for the first electrical wire 131a and the second electrical wire 131b. If one or both of the first and second electrical wires 131a, 131b detach from the plurality of guiding features 218 during operation or transportation of instrument 10, the first spine 208 will capture both the first and second electrical wire 131a, 131b and will guide both wires 131a, 131b to the shaft attachment 220. The first side 206a of the body 202 is placed adjacent to the perimeter of the housing 20. In an embodiment, the first side 206a of the body 202 is positioned to rest directly upon the perimeter of the housing 20. In another embodiment, the first side 206a of the body 202 is placed adjacent to the perimeter of housing 20 without contacting the perimeter thereof. The second side 206b of the body 202 includes a second spine 210 that perpendicularly protrudes therefrom. The spine 210 is placed adjacent to other internal components housed within the housing 20 and provides protection to the first electrical wire 131a and the second electrical wire 131b from any potential interference with or damage from the other internal components. The body 202 may be constructed of any appropriate plastic or other suitable material.

The housing attachment 212 is integrally formed within the wire guide 200, although other configurations may alternatively be provided. The housing attachment 212 includes a channel 214 and an aperture 216. Both the channel 214 and the aperture 216 are defined in the body 202 of the wire guide 200. Channel 214 and aperture 216 are interconnected in that channel 214 and aperture 216 are in direct communication with one another. Aperture 216 is configured to accept a protrusion 21 of the housing 20, which extends from housing 20 inwardly into the cavity defined within housing 20. The wire guide 200 is secured to the housing 20 by the interaction between protrusion 21 and aperture 216 of the housing attachment 212. The protrusion 21 may be positioned within the aperture 216 via sliding through channel 214 or via direct insertion therein. The wire guide 200 remains in a desired position once the protrusion 21 extends through the aperture 216. In another embodiment, the wire guide 200 includes multiple housing attachments 212, which may be integrally formed within the wire guide 200 at designated locations that register with locations of other protrusions of the housing 20 to enable engagement similarly as with protrusion 21 and aperture 216, thus providing multiple attachment points along wire guide 200.

Figure 5:
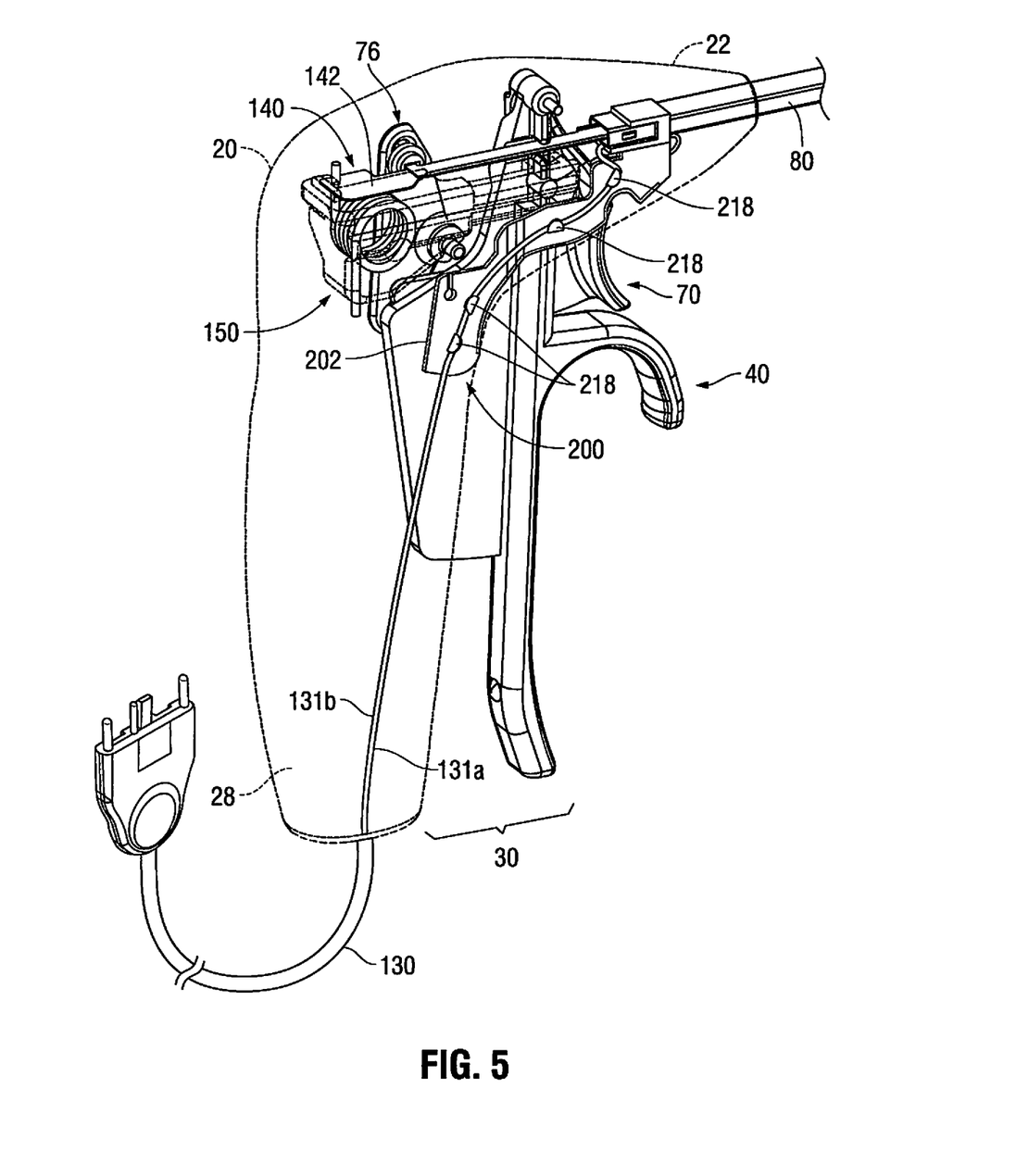
FIG. 5 is a rear, perspective view of the various components disposed within or coupled to the housing of the surgical instrument of FIG. 1.
Figure 6:
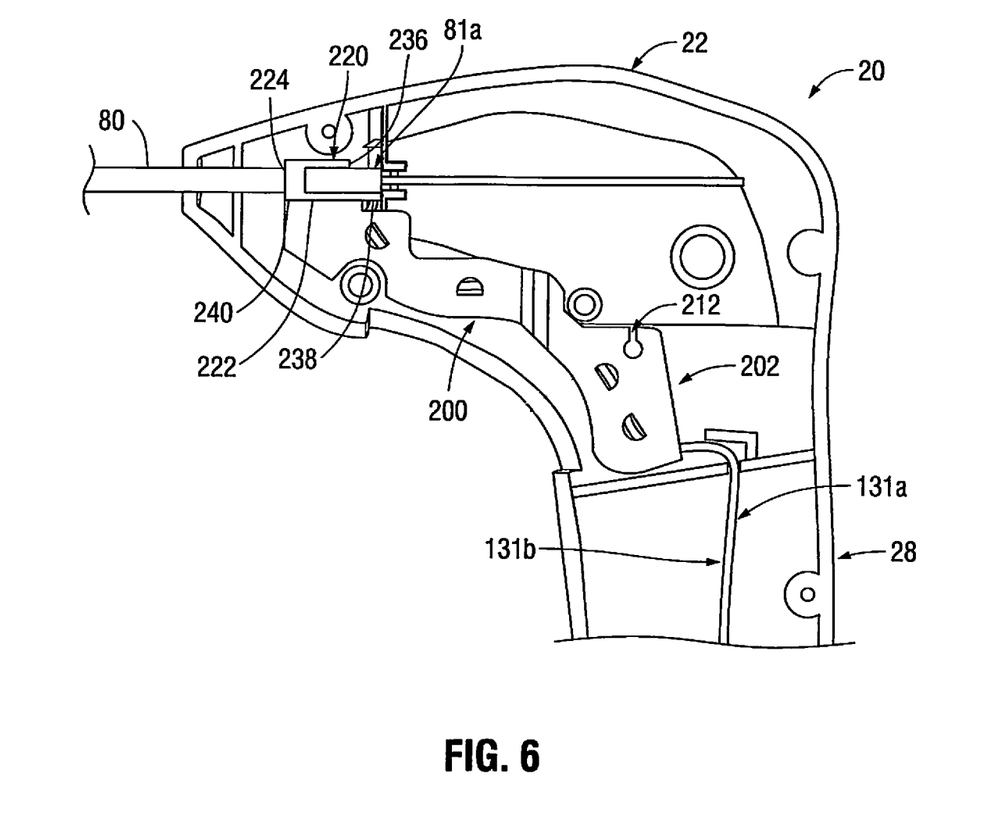
FIG. 6 is a side view of a proximal portion of the surgical instrument of FIG. 1 with components removed to illustrate a wire guide operably coupled to the housing and a shaft of the surgical instrument.

As mentioned above, the wire guide 200 includes a plurality of guiding features 218. In embodiments, each guiding feature 218 of the plurality of guiding features 218 takes the form of a square-shaped hook (FIG. 5). In such embodiments, the hook portion of each guiding feature 218 extends from the body 202 defining an area therebetween for receipt of the wire(s) 131a, 131b. In another embodiment, each guiding feature 218 of the plurality of guiding features takes the form of a C-shaped hook. In this embodiment, the hook portion of each guiding feature 218 extends from the body 202 to similarly define an area for receipt of the wire(s) 131a, 131b. In yet another embodiment, each guiding feature 218 of the plurality of guiding features 218 takes the form of a double U-shaped snap lock. In this embodiment, each double U-shaped snap lock includes three spaced-apart protrusions that extend perpendicular from the body 202. Two spaces between the three spaced-apart protrusions are each configured to secure one of the first and second electrical wires 131a, 131b in a serpentine fashion. Each guiding feature 218 is positioned in relation to one another to allow an appropriate amount of space between each guiding feature 218 while providing support for the first and second electrical wire 131a, 131b.

In embodiments, each guiding feature 218 is integrally formed with the wire guide 200. Additionally, in embodiments, each guiding feature 218 is configured to secure both the first and second electrical wires 131a and 131b to designated locations corresponding to the positions of guiding features 218 on the wire guide 200 such that the plurality of guiding features 218 provide guidance for both the first and second electrical wires 131a, 131b from the fixed handle portion 28 of housing 20, through the barrel portion 22 of housing 20, to the shaft attachment 220, as detailed further below.

Figure 9A:
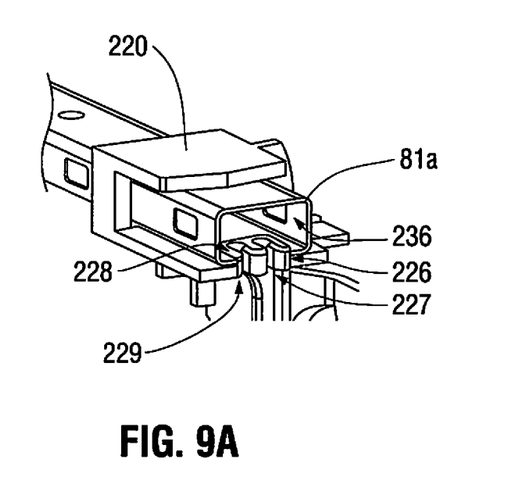
FIG. 9a is a top, perspective view of a shaft attachment portion of the wire guide of FIG. 6 operably coupled to a proximal portion of the shaft of the surgical instrument of FIG. 1.
Figure 9B:
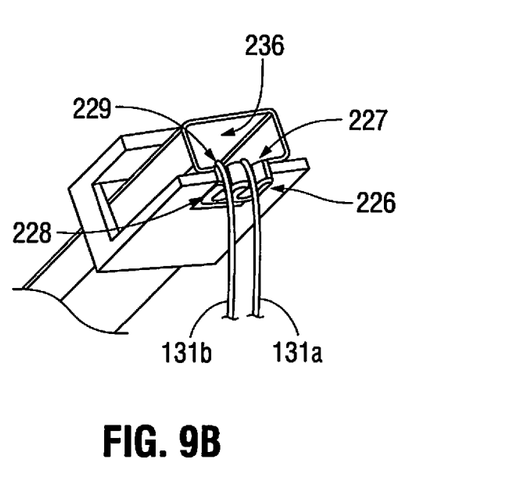
FIG. 9b is a bottom, perspective view of the shaft attachment portion of FIG. 9a operably coupled to a proximal portion of the shaft of the surgical instrument of FIG. 1.

Shaft attachment 220 includes a proximal end portion 222, a distal end portion 224, a first wire snap feature 226, a second wire snap feature 228, and a shaft passageway 236. The first wire snap feature 226 and the second wire snap feature 228 are defined in the proximal end portion 222 of the shaft attachment 220 and each includes a channel 227, 229, respectively. Each channel 227, 229 is defined in the proximal end portion 222 of the shaft attachment 220. Further, channel 227 is generally parallel to channel 229 with a finger 234 separating them. Both channels 227 and 229 are similarly configured, with channel 227 configured to secure the first electrical wire 131a to the shaft attachment 220 while channel 229 is configured to secure the second electrical wire 131b to the shaft attachment 220. The first and second wire snap features 226, 228 both separate and guide the first and second electrical wire 131a, 131b into shaft 80 and to the electrically-conductive plate 132 of each jaw member 110, 120 for electrical connection therewith. Wires 131a, 131b are inserted through wire snap features 226, 228, respectively, flexing snap features 226, 228 to permit passage of wires 131a, 131b into channels 227, 229, respectively. Once wires 131a, 131b are positioned within channels 227, 229, respectively, snap features 226, 228 are returned to their at-rest positions securing wires 131a, 131b within channels 227, 229, respectively, and inhibiting backing-out of wires 131a, 131b.

Shaft passageway 236 includes a first end portion 238, a second end portion 240, and a lumen 242 extending therethrough. First end portion 238 of the shaft passageway 236 is formed adjacent to the first and second wire snap features 226, 228. The lumen 242 is configured to receive the proximal end portion 81a of the shaft 80 to engage wire guide 200 therewith such that the proximal end portion 81a of shaft 80 is aligned with the first and second wire snap features 226, 228 in manner that allows the first and second electrical wire 131a, 131b to first be secured within the snap features 226, 228 and then enter the proximal end portion 81a of the shaft 80. The proximal end portion 81a of the shaft 80 may define cut-outs 83a, 83b positioned adjacent to the first and second wire snap features 226, 228 to facilitate passage of wires 131a, 131b into lumen 82 of shaft 80. Cut-outs 83a, 83b may be separate from one another or may be portions of a common cut-out defined within shaft 80. With or without cut-outs 83a, 83b wire guide 200 inhibits wires 131a, 131b from rubbing on or otherwise contacting the proximal edge of shaft 80, thus inhibiting cutting or damaging wires 131a, 131b thereby.

As mentioned above, the wire guide 200 guides first electrical wire 131a and second electrical wire 131b through the housing 20 in order to operably couple a generator, energy activation assembly 190, and end effector assembly 100 with one another to enable the selective supply of energy to the end effector assembly 100. An electrosurgical cable 130 provides a connection between the generator and the housing 20 (FIG. 1) and includes a lumen (not shown) that houses the first and second electrical wires 131a, 131b. Housing 20 includes an aperture (not directly illustrated) formed in the fixed handle portion 28. The electrosurgical cable 130 and first and second electrical wire 131a, 131b enter the housing 20 via this aperture. As detailed above, the first and second electrical wire 131a, 131b are guided through the housing 20 by the plurality of guiding features 218 of the wire guide 200 such that the wires 131a, 131b are kept away from the movable components disposed within housing 20 and/or other components that may damage wires 131a, 131b and/or may be interfered with by wires 131a, 131b. The first and second wire snaps 226, 228 route, in secure and separate relation, the first and second electrical wire 131a, 131b, respectively, from housing 20 into shaft 80. More specifically, the proximal end portion 81a of shaft 80 connects to the wire guide 200 via the shaft passageway 236 of the shaft attachment 220 such that the first and second electrical wires 131a, 131b enter the shaft 80 separately and out of the way of the other components extending through shaft 80 such that wires 131a, 131b remain separate and out of the way through the shaft 80, ultimately connecting to the electrically-conductive plates 132 of jaw members 110, 120, respectively.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a housing;
   a shaft extending distally from the housing and defining a lumen therethrough and a longitudinal axis;
   an end effector assembly disposed at a distal end portion of the shaft, the end effector assembly including a first electrically-conductive tissue-treating surface;
   a first electrical wire extending from the housing, through the shaft, and into electrical communication with the first electrically-conductive tissue-treating surface, the first electrical wire adapted to connect to a source of energy and configured to supply energy to the first electrically-conductive tissue-treating surface; and
   a wire guide disposed within the housing and engaged about a proximal portion of the shaft within the housing, the wire guide configured to guide the first electrical wire from the housing into the shaft, the wire guide including:
   a shaft attachment defining a passageway therethrough, the shaft having a proximal end received in the passageway; and
   a first wire snap feature disposed within the passageway of the shaft attachment and configured to secure a portion of the first electrical wire to the wire guide and direct the first electrical wire into the shaft, wherein the first electrical wire has a first portion extending perpendicularly relative to the longitudinal axis of the shaft, a bent second portion disposed within the first wire snap feature, and a third portion extending distally relative to the first and second portions and through the shaft, such that the first and third portions of the first electrical wire are perpendicular to one another and disposed on opposite sides of the first wire snap feature.

2. The surgical instrument of claim 1, wherein the wire guide includes at least one guiding feature configured to receive the first electrical wire and guide the first electrical wire along the wire guide.

3. The surgical instrument according to claim 2, wherein the wire guide includes a plurality of guiding features spaced-apart on the wire guide.

4. The surgical instrument of claim 1, wherein the shaft attachment has a proximal end portion and distal end portion, wherein the proximal end portion of the shaft attachment includes the first wire snap feature.

5. The surgical instrument of claim 1, further including a second electrical wire extending from the housing, through the shaft, and into electrical communication with a second electrically-conductive tissue-treating surface of the end effector assembly, the second electrical wire adapted to connect to a source of energy and configured to supply energy to the second electrically-conductive tissue-treating surface, wherein the wire guide is configured to guide the second electrical wire from the housing into the shaft.

6. The surgical instrument according to claim 5, wherein the wire guide includes at least one guiding feature, each guiding feature configured to receive each of the first and second electrical wires.

7. The surgical instrument according to claim 6, wherein the wire guide includes a second wire snap feature, the first wire snap feature configured to receive the first electrical wire and the second wire snap feature configured to receive the second electrical wire.

8. The surgical instrument according to claim 7, wherein the first and second wire snap features are spaced-apart to maintain the first and second electrical wires in spaced-apart relation in the vicinity of the first and second wire snap features.

9. The surgical instrument of claim 8, wherein the first and second wire snap features each define a channel in direct communication with an interior of the proximal end of the shaft.

10. The surgical instrument of claim 1, wherein the wire guide further includes a housing attachment, the housing attachment engaging the wire guide to the housing.

11. The surgical instrument of claim 1, wherein the housing includes a longitudinally-extending barrel portion, and a fixed handle portion extending perpendicularly from the barrel portion, and the wire guide has a proximal portion aligned with the fixed handle portion, and a distal portion aligned with the barrel portion.

12. A surgical instrument, comprising:
a housing;
a shaft extending distally from the housing and defining a lumen therethrough;
an end effector assembly disposed at a distal end portion of the shaft;
a first electrical wire extending from the housing, through the shaft, and into electrical communication with the end effector assembly; and
a wire guide disposed within the housing, the wire guide including:
a body including a proximal end portion and a distal end portion;
a plurality of spaced-apart wire guiding features disposed on the body between the proximal and distal end portions thereof;
a shaft attachment disposed at the distal end portion of the body, the shaft attachment defining a passageway therethrough, the shaft having a proximal end received in the passageway; and
a first wire snap feature disposed on the shaft attachment and configured to secure a portion of the first electrical wire to the wire guide and direct the first electrical wire into the shaft, wherein the plurality of spaced-apart wire guiding features are configured to guide the first electrical wire along the body of the wire guide from the proximal end portion thereof to the distal end portion thereof, the body, the plurality of spaced-apart wire guiding features, the shaft attachment, and the first wire snap feature of the wire guide are integrally formed with one another, wherein the proximal end of the shaft has a bottom wall defining a cutout having the first electrical wire extending therethrough.

13. The surgical instrument of claim 12, further including a second electrical wire extending from the housing, through the shaft, and into electrical communication with the end effector assembly, wherein the wire guide is configured to guide the second electrical wire from the housing into the shaft.

14. The surgical instrument of claim 13, wherein the plurality of spaced-apart wire guiding features is configured to receive each of the first and second electrical wires.

15. The surgical instrument of claim 14, wherein the wire guide includes a second wire snap feature, wherein the first wire snap feature is configured to receive the first electrical wire and the second wire snap feature is configured to receive the second electrical wire.

16. The surgical instrument of claim 15, wherein the first and second wire snap features are spaced-apart to maintain the first and second electrical wires in spaced-apart relation to the vicinity of the first and second wire snap features.

17. The surgical instrument of claim 12, wherein the wire guide further includes a housing attachment, the housing attachment engaging the wire guide to the housing.

\* \* \* \* \*